(12) United States Patent
Copp-Howland et al.

(10) Patent No.: US 8,428,751 B2
(45) Date of Patent: Apr. 23, 2013

(54) ELECTRODE DELIVERY SYSTEM

(75) Inventors: Warren Copp-Howland, Chicopee, MA (US); Erick Garstka, Westfield, MA (US); David Selvitelli, Suffield, CT (US); Kathleen Tremblay, Westfield, MA (US); Caroline Gasiorski, Feeding Hills, MA (US)

(73) Assignee: Covidien LP, Mansfield, MA (US)

( * ) Notice: Subject to any disclaimer, the term of this patent is extended or adjusted under 35 U.S.C. 154(b) by 268 days.

(21) Appl. No.: 12/886,926

(22) Filed: Sep. 21, 2010

(65) Prior Publication Data

US 2011/0230925 A1    Sep. 22, 2011

Related U.S. Application Data

(60) Provisional application No. 61/315,159, filed on Mar. 18, 2010.

(51) Int. Cl.
*A61N 1/04* (2006.01)
(52) U.S. Cl.
USPC .......................................................... 607/142
(58) Field of Classification Search ................ 607/5, 67, 607/115, 142, 148
See application file for complete search history.

(56) References Cited

U.S. PATENT DOCUMENTS

| 4,779,630 | A | * | 10/1988 | Scharnberg et al. | .......... | 607/142 |
|---|---|---|---|---|---|---|
| 5,462,157 | A | * | 10/1995 | Freeman et al. | .............. | 206/210 |
| 5,797,969 | A | | 8/1998 | Olson et al. | | |
| 5,817,151 | A | | 10/1998 | Olson et al. | | |
| 6,083,246 | A | | 7/2000 | Stendahl et al. | | |
| 6,115,638 | A | | 9/2000 | Groenke | | |
| 6,314,320 | B1 | | 11/2001 | Powers et al. | | |
| 6,321,113 | B1 | | 11/2001 | Parker et al. | | |
| 6,556,864 | B1 | | 4/2003 | Picardo et al. | | |
| 6,662,046 | B2 | | 12/2003 | Hansen | | |
| 6,662,056 | B2 | * | 12/2003 | Picardo et al. | ................. | 607/142 |
| 6,675,051 | B2 | | 1/2004 | Janae et al. | | |
| 6,872,080 | B2 | | 3/2005 | Pastrick et al. | | |
| 6,874,621 | B2 | * | 4/2005 | Solosko et al. | ............... | 206/210 |
| 6,928,322 | B2 | | 8/2005 | Yerkovich et al. | | |
| 6,948,295 | B2 | | 9/2005 | Biggins | | |

(Continued)

FOREIGN PATENT DOCUMENTS

WO    WO 2007/084442 A2    7/2007

OTHER PUBLICATIONS

Lifesaving Products—Laerdal Products Catalogue 2008-2009; 148 Pages; (date of priority prior to filing of the present application).

(Continued)

*Primary Examiner* — Brian T Gedeon
(74) *Attorney, Agent, or Firm* — Lisa E. Winsor, Esq.

(57) ABSTRACT

According to an aspect of the present disclosure, an automatic external defibrillator configured to deliver electrical pulses and/or shocks to a heart of a patient during a cardiac emergency is provided and includes a housing supporting an electrical connector; a defibrillator electrode delivery system supported on the housing; and a pair of defibrillation electrode pads supported by the defibrillator electrode delivery system. Each of the pair of defibrillation electrode pads is pre-connected to the electrical connector of the housing. A hydrogel layer of each defibrillation electrode pad is retained by the defibrillator electrode delivery system in such a manner so as to reduce a moisture vapor transmission rate thereof.

23 Claims, 3 Drawing Sheets

U.S. PATENT DOCUMENTS

| | | |
|---|---|---|
| 6,965,799 B2 | 11/2005 | Nova et al. |
| 6,969,259 B2 | 11/2005 | Pastrick et al. |
| 7,069,074 B2 | 6/2006 | Covey et al. |
| 7,072,712 B2 | 7/2006 | Kroll et al. |
| 7,231,247 B2 | 6/2007 | Faller et al. |
| 7,236,823 B2 | 6/2007 | Herbert |
| RE40,365 E | 6/2008 | Kirchgeorg et al. |
| 7,453,354 B2 | 11/2008 | Reiter et al. |
| 7,457,662 B2 | 11/2008 | Nassif |
| 7,463,923 B2 | 12/2008 | Brewer et al. |
| 7,489,972 B2 | 2/2009 | Denney et al. |
| 7,792,577 B2 | 9/2010 | Hamilton et al. |
| 7,797,044 B2 | 9/2010 | Covey et al. |
| 2006/0058846 A1 | 3/2006 | Smirles et al. |
| 2007/0255382 A1 | 11/2007 | Meyer et al. |
| 2009/0227857 A1 | 9/2009 | Rowe et al. |
| 2009/0270709 A1 | 10/2009 | Copp et al. |
| 2009/0270710 A1 | 10/2009 | Copp et al. |
| 2009/0281585 A1 | 11/2009 | Katzman et al. |
| 2010/0072060 A1 | 3/2010 | Copp-Howland |

OTHER PUBLICATIONS

International Search Report corresponding to European Application No. EP 11 15 7002.4, completed on May 26, 2011 and mailed on Jun. 8, 2011; 6 pages.

* cited by examiner

ELECTRODE DELIVERY SYSTEM

CROSS-REFERENCE TO RELATED APPLICATIONS

The present application claims the benefit of and priority to U.S. Provisional Application Ser. No. 61/315,159, filed on Mar. 18, 2010, entitled "Electrode Delivery System," the entire content of which is being incorporated herein by reference.

BACKGROUND

1. Technical Description

The present disclosure relates to defibrillator and defibrillation electrodes and, more particularly, to systems, methods and packages to facilitate the use and connection of defibrillation electrodes to a defibrillator prior to the electrodes being used on a patient, while allowing the electrodes to maintain a sufficient amount of moisture to be able to properly function.

2. Background of Related Art

Electrodes which are typically used in medical applications generally include a conductor and a connector. The connector is attached at one end to the conductor and includes a plug at the other end to be plugged into a defibrillator or other device. The conductor is often covered or coated in a conductive gel, which enhances its ability to adhere to a patient's skin. When the conductive gel becomes too dry, it may lose its ability to adhere to a patient or demonstrate excessively high contact impedance. To prevent the conductive gel from drying out, the electrode may be stored in a package prior to use.

In a medical setting, there are often a variety of different defibrillators and electrodes at a clinician's disposal and it is not uncommon for several of the defibrillators and electrodes to have different manufacturers. Compatibility among defibrillators (or other medical devices) and electrodes of different brands is often lacking, which can cause confusion as to which particular electrode to use with a given defibrillator. Thus, clinicians open electrode packages to determine if the electrode (or electrode plug) is compatible with the defibrillator. If the electrode (or electrode plug) is not compatible with the defibrillator, the opened electrode is set aside and the clinician would open a different packaged electrode. As can be appreciated, testing electrodes in this fashion leads to waste, as the electrodes that are not compatible are likely to become too thy if not used in a timely fashion.

Further, in preparation for an emergency situation, clinicians may perform as many steps as possible before such an emergency situation arises. For example, a clinician may prepare a defibrillator by "pre-connecting" a compatible electrode to the defibrillator. Pre-connecting a compatible electrode to a defibrillator prevents rapid diffusion of moisture from the conductive gel, and reduces the number of steps that are needed to take place during an actual emergency.

In many instances, when an emergency situation arises at a public location remote from a medical facility, Automatic External Defibrillators (AED's) may generally be available for use on the individual experiencing the medical emergency. An AED is a portable electronic device that automatically diagnoses the potentially life threatening cardiac arrhythmias of ventricular fibrillation and ventricular tachycardia in a patient, and is able to treat them through defibrillation, the application of electrical therapy which stops the arrhythmia, allowing the heart to reestablish an effective rhythm.

A need exists for a system of delivering electrodes to a patient that is easier to use and more simple to use, and that reduces the time required for a user of the AED to set-up the AED.

SUMMARY

The present disclosure relates to systems, methods and packages to facilitate the use and connection of defibrillation electrodes to a defibrillator prior to the electrodes being used on a patient, while allowing the electrodes to maintain a sufficient amount of moisture to be able to properly function.

According to an aspect of the present disclosure, an automatic external defibrillator configured to deliver electrical pulses and/or shocks to a heart of a patient during a cardiac emergency is provided and includes a housing supporting an electrical connector; a defibrillator electrode delivery system supported on the housing; and a pair of defibrillation electrode pads supported by the defibrillator electrode delivery system. Each of the pair of defibrillation electrode pads is pre-connected to the electrical connector of the housing. A hydrogel layer of each defibrillation electrode pad is retained by the defibrillator electrode delivery system in such a manner so as to reduce a moisture vapor transmission rate thereof.

The defibrillator electrode delivery system may include an electrode receiving surface defined on an outer surface of the housing, and wherein each defibrillation electrode pad is adhered to the electrode receiving surface of the housing.

The electrode receiving surface of the housing may be coated with a release material.

The defibrillator electrode delivery system may include a pair of spaced apart brackets extending from the housing; and a release liner sized to extend across the space defined by the pair of brackets, wherein the brackets are configured to retain the release liner in close proximity to the housing, and wherein each defibrillation electrode pad is adhered to a surface of the release liner.

The defibrillator electrode delivery system may include a carrier flap having a side edge connected to the housing, wherein an electrode pad of the pair of defibrillation electrode pads is adhered to a surface of a respective side of the carrier flap.

The defibrillator electrode delivery system may include a hinge connecting the side edge of the carrier flap to the housing. The defibrillator electrode delivery system may include a clamp connecting the side edge of the carrier flap to the housing.

For each of the pair of defibrillation electrode pads, the defibrillator electrode delivery system may include a two-part fastener member selectively securing each of the pair of defibrillation electrode pads to the housing, wherein a first part of the two-part fastener is secured to the housing and a second part of the two-part fastener is secured to a backing layer of each electrode pad.

Each defibrillation electrode pad may include a backing layer, a substrate overlying the backing layer, a hydrogel overlying the substrate and a liner overlying the hydrogel.

The defibrillator may further include a pair of contact pads supported in a surface of the housing, wherein each contact pad is electrically connected to the connector of the housing by a respective electrical connector, and wherein each electrode pad of the pair of defibrillation electrode pads is adhered to a surface of the housing so as to be in contact with a respective contact pad.

The defibrillator may be configured to perform checks of an impedance of the electrode pads when the electrode pads are in contact with the contact pads.

The defibrillator may be configured to automatically power-up upon a separation of the pair of defibrillation electrode pads from the contact pads.

The defibrillator may be configured to automatically power-up upon a separation of at least one of the pair of defibrillation electrode pads from the contact pads.

An impedance reading by the contact pads may be changed upon the separation of at least one of the pair of defibrillation electrode pads from the contact pad resulting in the automatic power-up of the defibrillator.

The defibrillator electrode delivery system may include a release liner supported on a surface of housing, and wherein the pair of defibrillation electrode pads may include an apex electrode and a sternum electrode adhered to a surface of the release liner, wherein the apex electrode includes a tab that projects from a perimeter of the release liner.

The sternum electrode may include a tab, and wherein the tab of the sternum electrode is exposed following a separation of the apex electrode from the release liner.

The release liner may be slidably supported on the surface of the housing, wherein as the tab of the apex electrode is pulled in a direction substantially parallel to a plane of the release liner, the release liner is slid in the direction of the pull and separated from the apex electrode.

In use, when the apex electrode is separate from the release liner, the tab of the sternum electrode may be exposed.

According to another aspect of the present disclosure, an automatic external defibrillator configured to deliver electrical pulses and/or shocks to a heart of a patient during a cardiac emergency is provided and includes a housing supporting an electrical connector, a battery and high voltage circuitry; and a pair of defibrillation electrode pads supported on the housing, wherein each of the pair of defibrillation electrode pads is pre-connected to the electrical connector of the housing, and wherein each defibrillation electrode pad is in electrical communication with the battery and the high voltage circuitry. The defibrillator is automatically activated by a separation of at least one of the pair of defibrillation electrode pads from the housing. A hydrogel layer of each defibrillation electrode pad is retained by the housing in such a manner so as to reduce a moisture vapor transmission rate thereof.

The defibrillator may further include a pair of contact pads supported in a surface of the housing, wherein each contact pad is electrically connected to the connector of the housing by a respective electrical connector, and wherein each electrode pad of the pair of defibrillation electrode pads is disposed on a surface of the housing so as to be in contact with a respective contact pad.

The defibrillator may be configured to perform checks of an impedance of the electrode pads when the electrode pads are in contact with the contact pads.

The defibrillator may be configured to automatically power-up upon a separation of the pair of defibrillation electrode pads from the contact pads.

The defibrillator may be configured to automatically power-up upon a separation of at least one of the pair of defibrillation electrode pads from the contact pads.

An impedance reading by the contact pads may be changed upon the separation of at least one of the pair of defibrillation electrode pads from the contact pad resulting in the automatic power-up of the defibrillator.

BRIEF DESCRIPTION OF THE DRAWINGS

Various embodiments of electrode delivery systems are described herein with reference to the drawings wherein.

DETAILED DESCRIPTION

Figure 1:
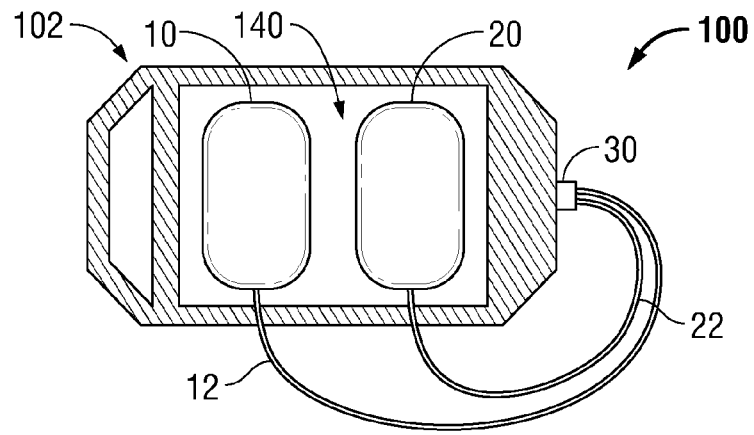
FIG. 1 is a top, plan view of a defibrillator electrode delivery system according to an embodiment of the present disclosure.

Embodiments of the presently disclosed defibrillator electrode delivery system will now be described in detail with reference to the drawing figures wherein like reference numerals identify similar or identical elements.

As illustrated in FIG. 1, a defibrillator electrode delivery system, according to an embodiment of the present disclosure, is generally designated as 100. Defibrillator electrode delivery system 100 includes an automatic external defibrillator (AED) 102 defining a surface 140 configured to store or retain a pair of electrode pads 10, 20. Electrode pads 10, 20 are electrically connectable to or pre-connected to AED 102 via respective lead wires 12, 22 joined at a connector 30.

Surface 140 is coated with a release material to selectively adhere electrode pads 10, 20 thereto and to facilitate the removal of electrode pads 10, 20 therefrom when needed. For example, the release material may be Teflon, silicone, and combinations thereof.

In this configuration, a gel layer of each electrode pad 10, 20 has a reduced tendency to dry-out. Due to the adherence of the electrode pads 10, 20 to surface 140 of AED 102, no special packaging is required that reduces a moisture vapor transmission rate (MVTR) of the electrode pads 10, 20.

Figure 2:
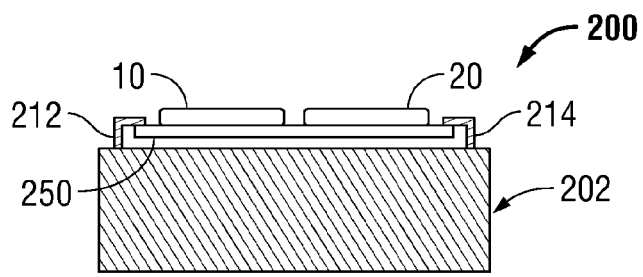
FIG. 2 is a side, elevational view of a defibrillator electrode delivery system according to another embodiment of the present disclosure.

As illustrated in FIG. 2, a defibrillator electrode delivery system, according to another embodiment of the present disclosure, is generally designated as 200. Defibrillator electrode delivery system 200 includes an automatic external defibrillator (AED) 202 having a pair of spaced apart brackets 212, 214 supported on a surface thereof. Defibrillator electrode delivery system 200 is configured to store or retain a pair of electrode pads 10, 20 that are supported on a release liner 250. Brackets 212, 214 are spaced apart an amount sufficient to engage, capture and/or lock down on release liner 250 to thereby maintain electrode pads 10, 20 secured to AED 202. Electrode pads 10, 20 are electrically connected to AED 202 via respective lead wires (not shown) joined at a connector (not shown).

In this configuration, a gel layer of each electrode pad 10, 20 has a reduced tendency to dry-out. Due to the adherence of the electrode pads 10, 20 to release liner 250, no special packaging is required that reduces a moisture vapor transmission rate (MVTR) of the electrode pads 10, 20.

Figures 3A, 3B:
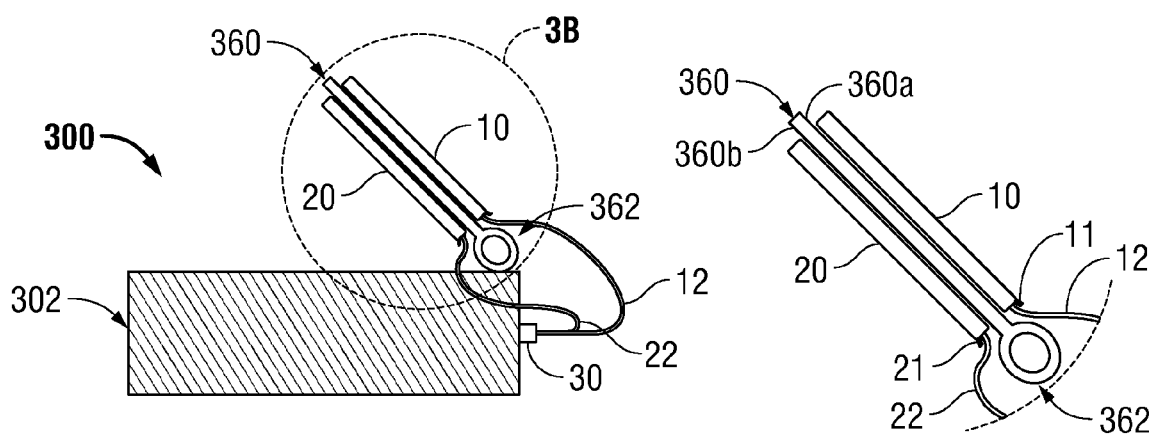
FIG. 3A is a side, elevational view of a defibrillator electrode delivery system according to a further embodiment of the present disclosure.
FIG. 3B is an enlarged view of the indicated area of detail of FIG. 3A.

As illustrated in FIGS. 3A and 3B, a defibrillator electrode delivery system, according to a further embodiment of the present disclosure, is generally designated as 300. Defibrillator electrode delivery system 300 includes an automatic external defibrillator (AED) 302 having a carrier flap or page 360 hingedly connected thereto via a hinge member 362. Defibrillator electrode delivery system 300 is configured to store or retain a pair of electrode pads 10, 20 that are supported on a front side, a back side and/or on opposed sides 360a, 360b of flap 360 (as shown in FIGS. 3A and 3B). As shown in FIG. 3B, each electrode pad 10, 20 may include a respective pull tab 11, 21 to facilitate the removal of electrode pads 10, 20 from flap 360. Electrode pads 10, 20 are electrically connectable to or pre-connected to AED 302 via respective lead wires 12, 22 joined at a connector 30.

In this configuration, a gel layer of each electrode pad 10, 20 has a reduced tendency to dry-out. Due to the adherence of the electrode pads 10, 20 to flap 360, no special packaging is required that reduces a moisture vapor transmission rate (MVTR) of the electrode pads 10, 20.

Figure 4:
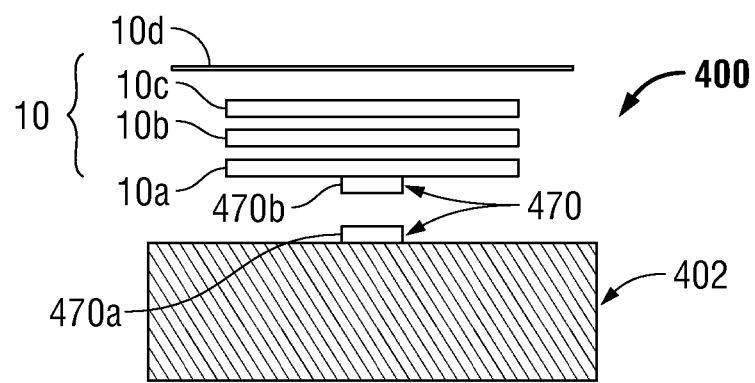
FIG. 4 is a side, elevational view, with parts separated, of a defibrillator electrode delivery system according to yet another embodiment of the present disclosure.

As illustrated in FIG. 4, a defibrillator electrode delivery system, according to still another embodiment of the present disclosure, is generally designated as 400. Defibrillator electrode delivery system 400 includes an automatic external defibrillator (AED) 402 having a two-part fastener member 470 associated therewith for selectively securing a pair of electrode pads thereto (only one electrode pad 10 being shown). Two-part fastener member 470 includes a first part 470a secured to AED 402 and a second part 470b secured to a backing layer 10a of electrode pad 10. Electrode 10 includes a conductive and/or non-conductive substrate 10b overlying backing layer 10a, on a side opposite the second part 470b of the two-part fastener member 470. Electrode 10 further includes a gel or hydrogel layer 10c overlying substrate 10b, and a liner 10d overlying gel or hydrogel layer 10c.

Two-part fastener member 470 may be in the form of a hook and loop type fastener where one of the first part 470a and the second part 470b is the hook portion and the other of the first part 470a and the second part 470b is the loop portion. It is contemplated that the two-part fastener member 470 may include double-sided tape or the like.

In this configuration, a gel or hydrogel layer 10e of electrode pad 10 has a reduced tendency to dry-out. Due to the securement of the electrode pad 10 to AED 402 and to the provision of a liner 10d overlying gel or hydrogel layer 10c, no special packaging is required that reduces a moisture vapor transmission rate (MVTR) of the electrode pads.

Figure 5:
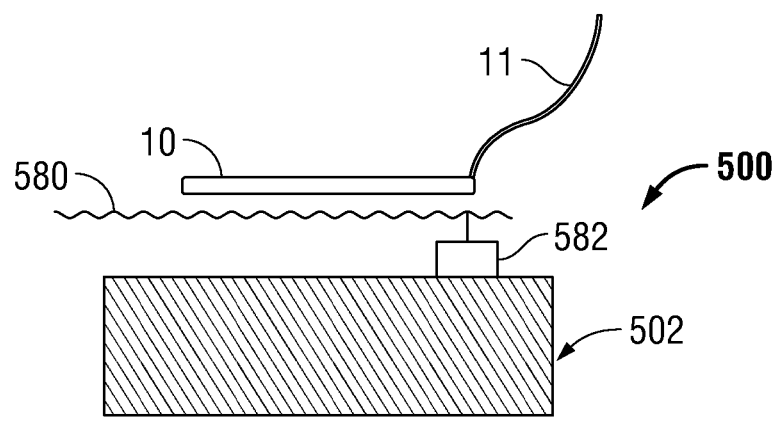
FIG. 5 is a side, elevational view of a defibrillator electrode delivery system according to still another embodiment of the present disclosure.

As illustrated in FIG. 5, a defibrillator electrode delivery system, according to another embodiment of the present disclosure, is generally designated as 500. Defibrillator electrode delivery system 500 includes an automatic external defibrillator (AED) 502 having a release liner 580 secured to a surface thereof via a clamp 582. Defibrillator electrode delivery system 500 is configured to store or retain at least one electrode pad 10 on a front side 580a of release liner 580. As shown in FIG. 5, electrode pad 10 may include a pull tab 11 to facilitate the removal of electrode pad 10 from release liner 580.

In this configuration, a gel layer of electrode pad 10 has a reduced tendency to dry-out. Due to the adherence of the electrode pad 10 to release liner 580, no special packaging is required that reduces a moisture vapor transmission rate (MVTR) of the electrode pads 10, 20.

Figure 6:
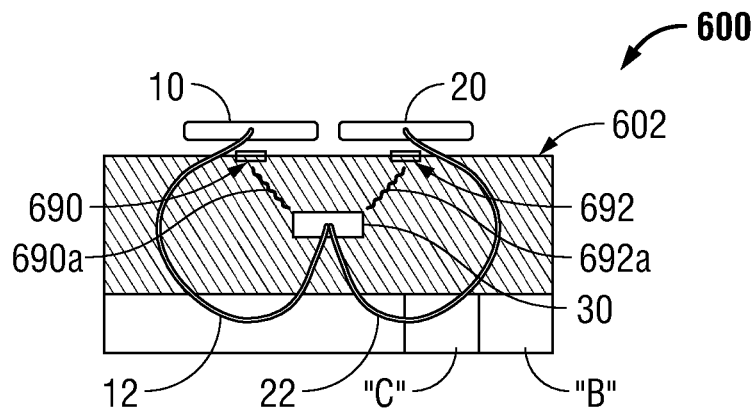
FIG. 6 is a side, elevational view of a defibrillator electrode delivery system according to another embodiment of the present disclosure.

As illustrated in FIG. 6, a defibrillator electrode delivery system, according to yet another embodiment of the present disclosure, is generally designated as 600. Defibrillator electrode delivery system 600 includes an automatic external defibrillator (AED) 602 including a pair of electrical contact points or pads 690, 692 disposed in a surface thereof. Defibrillator electrode delivery system 600 includes a pair of electrode pads 10, 20 electrically connectable to or pre-connected to AED 602 via respective lead wires 12, 22 joined at a connector 30. Electrode pads 10, 20 are also in contact with respective contact pads 690, 692. Each electrical contact pad 690, 692 is electrically connected to a respective electrical connector 690a, 692a which electrically interconnected to respective lead wires 12, 22 by way of connector 30.

In this manner, a first electrical circuit is defined which includes contact pad 690, a respective electrical connector 690a, connector 30, lead wire 12 and electrode pad 10. Also, a second electrical circuit is defined which includes contact pad 692, a respective electrical connector 692a, connector 30, lead wire 22 and electrode pad 20.

AED 602, as schematically shown in FIG. 6, includes a battery "B" and high voltage circuitry "C" disposed in a housing 602a thereof. The battery and the high voltage circuitry are electrically connected to connector 30 and/or electrical connectors 690a, 690b.

It is contemplated that as electrode pads 10, 20 are lifted or separated from AED 602, that electrode pads 10, 20 separate from contact pads 690, 692, altering an impedance or breaking a respective circuit therebetween, and thereby causing AED 602 to automatically begin to power-up or initialize (i.e., run an automated set-up process with readies AED 602 prior to use in a cardiac emergency). It is further contemplated that AED 602 is automatically powered-up upon a separation of any one of electrode pads 10, 20 from contact pads 690, 692 of AED 602.

Alternatively, or in addition to the automated set-up process, as so configured, an impedance check may be performed across each electrode pad 10, 20 to check an impedance of each electrode pad 10, 20 and determine if a moisture content of a gel layer of each electrode pad 10, 20 is acceptable for use thereof.

Figure 7:
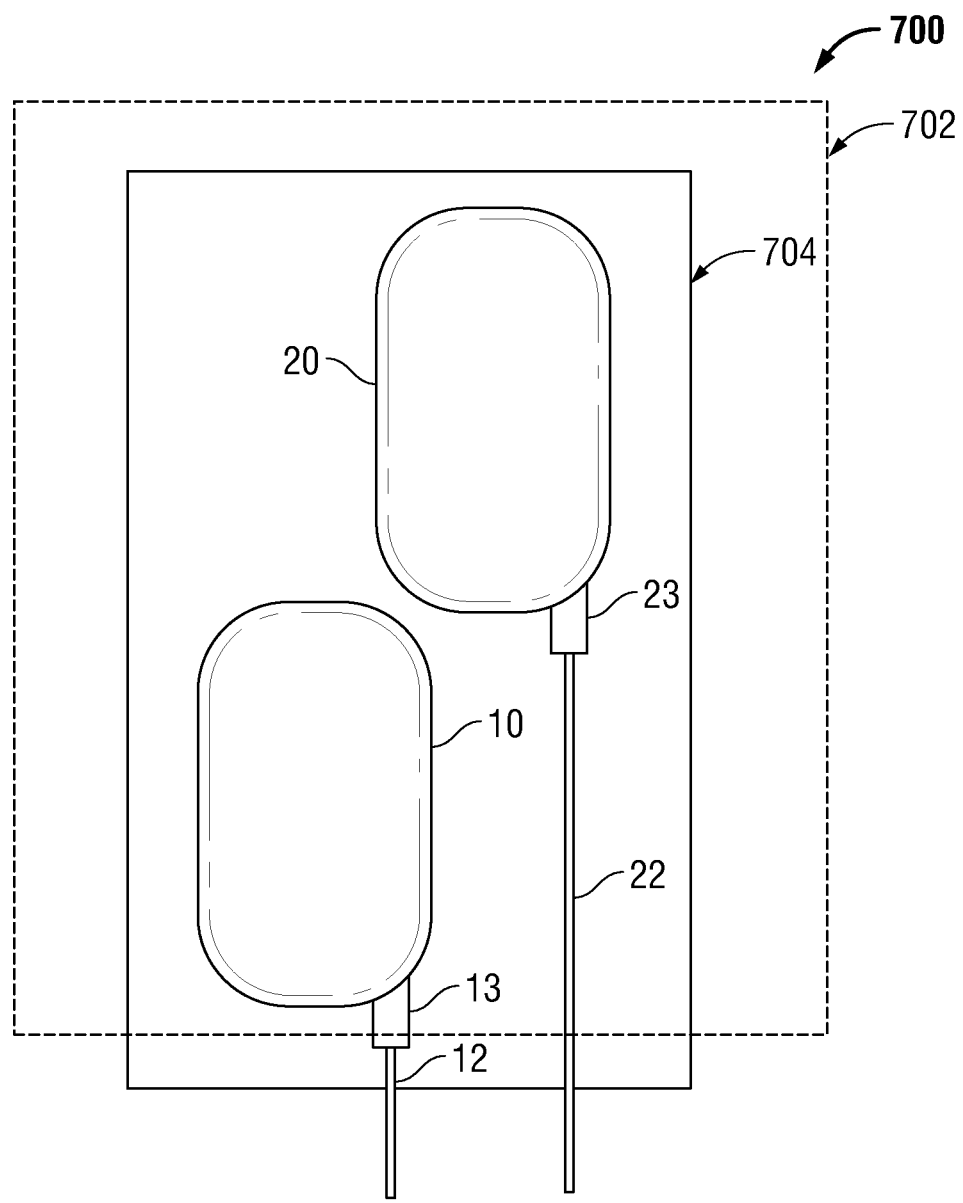
FIG. 7 is a top, plan view of a defibrillator electrode delivery system according to another embodiment of the present disclosure.

As illustrated in FIG. 7, a defibrillator electrode delivery system, according to still another embodiment of the present disclosure, is generally designated as 700. Defibrillator electrode delivery system 700 includes an automatic external defibrillator (AED) 702 including a pair of electrode pads, an apex electrode pad 10 and a sternum electrode pad 20. Electrode pads 10, 20 are electrically connectable to or pre-connected to AED 702 via respective lead wires 12, 22. Apex electrode pad 10 includes a pull tab 13 that projects from or extends from a perimeter of a box or liner 704 disposed on AED 702, which retains electrode pads 10, 20. Electrode pads 10, 20 are arranged on box or liner 704 such that, as apex electrode pad 10 is peeled off of box or liner 704, liner 704 rolls forward and exposes a pull tab 23 of sternum electrode pad 20 so that the sternum electrode pad 20 is ready to be removed from liner 704 after placement of apex electrode pad 10 is placed against the patient.

In accordance with any of the embodiments of the present disclosure described above, it is contemplated that as electrode pads 10, 20 are removed from or separated from the surface of the AED, that the AED may automatically begin to power-up.

Electrode pads configured for use with any of the electrode delivery systems disclosed herein are shown and described in International Patent Application Serial No. PCT/US2007/010060, filed Apr. 27, 2007, in U.S. patent application Ser. No. 12/237,803, filed on Sep. 25, 2008, and U.S. Patent Application Publication No. 2009/0227857, filed on Mar. 6, 2008, the entire content of each of which being incorporated herein by reference.

An example of a suitable polymer which may be utilized in the electrode pads disclosed herein includes RG-63B hydrogel, commercially available from Tyco Healthcare Group d/b/a/Covidien. Other suitable hydrogels include those disclosed in U.S. Patent Application Publication No. 2009/0270709, filed on Oct. 30, 2009, and U.S. Patent Application Publication No. 2009/0270710, filed on Oct. 30, 2009, the entire disclosures of each of which are incorporated by reference herein for all purposed.

It is to be understood that the foregoing description is merely a disclosure of particular embodiments and is in no way intended to limit the scope of the disclosure. Other possible modifications will be apparent to those skilled in the art and are intended to be within the scope of the present disclosure.

What is claimed is:

1. An automatic external defibrillator configured to deliver electrical pulses and/or shocks to a heart of a patient during a cardiac emergency, the defibrillator comprising:
    a housing supporting an electrical connector; and
    a pair of defibrillation electrode pads supported on the housing, wherein each of the pair of defibrillation electrode pads is pre-connected to the electrical connector of the housing, and wherein a hydrogel layer of each defibrillation electrode pad is configured to contact the housing in such a manner so as to reduce a moisture vapor transmission rate thereof.

2. The defibrillator according to claim 1, wherein an electrode receiving surface is defined on an outer surface of the housing, and wherein each defibrillation electrode pad is adhered to the electrode receiving surface of the housing.

3. The defibrillator according to claim 2, wherein the electrode receiving surface of the housing is coated with a release material.

4. The defibrillator according to claim 1, wherein, for each of the pair of defibrillation electrode pads, the housing includes:
    a two-part fastener member selectively securing each of the pair of defibrillation electrode pads to the housing, wherein a first part of the two-part fastener is secured to the housing and a second part of the two-part fastener is secured to a backing layer of each electrode pad.

5. The defibrillator according to claim 4, wherein each defibrillation electrode pad includes a backing layer, a substrate overlying the backing layer, a hydrogel overlying the substrate and a liner overlying the hydrogel.

6. An automatic external defibrillator configured to deliver electrical pulses and/or shocks to a heart of a patient during a cardiac emergency, the defibrillator comprising:
    a housing supporting an electrical connector, a battery and high voltage circuitry; and
    a pair of contact pads supported in a surface of the housing;
    a pair of defibrillation electrode pads supported on the housing, wherein each of the pair of defibrillation electrode pads is pre-connected to the electrical connector of the housing, and wherein each defibrillation electrode pad is in electrical communication with the battery and the high voltage circuitry;
    wherein the defibrillator is automatically activated by a separation of at least one of the pair of defibrillation electrode pads from the housing; and
    wherein a hydrogel layer of each defibrillation electrode pad is retained by the housing in such a manner so as to reduce a moisture vapor transmission rate thereof,
    wherein each contact pad is electrically connected to the connector of the housing by a respective electrical connector, and wherein each electrode pad of the pair of defibrillation electrode pads is disposed on a surface of the housing so as to be in contact with a respective contact pad.

7. The defibrillator according to claim 6, wherein the defibrillator is configured to perform checks of an impedance of the electrode pads when the electrode pads are in contact with the contact pads.

8. The defibrillator according to claim 6, wherein the defibrillator is configured to automatically power-up upon a separation of the pair of defibrillation electrode pads from the contact pads.

9. The defibrillator according to claim 6, wherein the defibrillator is configured to automatically power-up upon a separation of at least one of the pair of defibrillation electrode pads from the contact pads.

10. The defibrillator according to claim 9, wherein an impedance reading by the contact pads is changed upon the separation of at least one of the pair of defibrillation electrode pads from the contact pad resulting in the automatic power-up of the defibrillator.

11. An automatic external defibrillator configured to deliver electrical pulses and/or shocks to a heart of a patient during a cardiac emergency, the defibrillator comprising:
    a housing supporting an electrical connector;
    a pair of defibrillation electrode pads supported on the housing, wherein each of the pair of defibrillation electrode pads is pre-connected to the electrical connector of the housing, and wherein a hydrogel layer of each defibrillation electrode pad is retained by the housing in such a manner so as to reduce a moisture vapor transmission rate thereof;
    a pair of spaced apart brackets extending from the housing; and
    a release liner sized to extend across the space defined by the pair of brackets,
    wherein the brackets are configured to retain the release liner in close proximity to the housing, and wherein each defibrillation electrode pad is adhered to a surface of the release liner.

12. An automatic external defibrillator configured to deliver electrical pulses and/or shocks to a heart of a patient during a cardiac emergency, the defibrillator comprising:
    a housing supporting an electrical connector;
    a pair of defibrillation electrode pads supported on the housing, wherein each of the pair of defibrillation electrode pads is pre-connected to the electrical connector of the housing, and wherein a hydrogel layer of each defibrillation electrode pad is retained by the housing in such a manner so as to reduce a moisture vapor transmission rate thereof; and
    a carrier flap having a side edge connected to the housing, wherein an electrode pad of the pair of defibrillation electrode pads is adhered to a surface of a respective side of the carrier flap.

13. The defibrillator according to claim 12, wherein the housing includes a hinge connecting the side edge of the carrier flap to the housing.

14. The defibrillator according to claim 12, wherein the housing includes a clamp connecting the side edge of the carrier flap to the housing.

15. An automatic external defibrillator configured to deliver electrical pulses and/or shocks to a heart of a patient during a cardiac emergency, the defibrillator comprising:
    a housing supporting an electrical connector;
    a pair of defibrillation electrode pads supported on the housing, wherein each of the pair of defibrillation electrode pads is pre-connected to the electrical connector of the housing, and wherein a hydrogel layer of each defibrillation electrode pad is retained by the housing in such a manner so as to reduce a moisture vapor transmission rate thereof; and a pair of contact pads supported in a surface of the housing, each contact pad is electrically connected to the connector of the housing by a respective electrical connector, wherein each electrode pad of the pair of defibrillation electrode pads is adhered to a surface of the housing so as to be in contact with a respective contact pad.

16. The defibrillator according to claim 15, wherein the defibrillator is configured to perform checks of an impedance of the electrode pads when the electrode pads are in contact with the contact pads.

17. The defibrillator according to claim 15, wherein the defibrillator is configured to automatically power-up upon a separation of the pair of defibrillation electrode pads from the contact pads.

18. The defibrillator according to claim 15, wherein the defibrillator is configured to automatically power-up upon a separation of at least one of the pair of defibrillation electrode pads from the contact pads.

19. The defibrillator according to claim 18, wherein an impedance reading by the contact pads is changed upon the separation of at least one of the pair of defibrillation electrode pads from the contact pad resulting in the automatic power-up of the defibrillator.

20. An automatic external defibrillator configured to deliver electrical pulses and/or shocks to a heart of a patient during a cardiac emergency, the defibrillator comprising:

a housing supporting an electrical connector;

a release liner supported on a surface of housing; and a pair of defibrillation electrode pads supported on the housing, wherein each of the pair of defibrillation electrode pads is pre-connected to the electrical connector of the housing, and wherein a hydrogel layer of each defibrillation electrode pad is retained by the housing in such a manner so as to reduce a moisture vapor transmission rate thereof, wherein the pair of defibrillation electrode pads includes an apex electrode and a sternum electrode adhered to a surface of the release liner, wherein the apex electrode includes a tab that projects from a perimeter of the release liner.

21. The defibrillator according to claim 20, wherein the sternum electrode includes a tab, and wherein the tab of the sternum electrode is exposed following a separation of the apex electrode from the release liner.

22. The defibrillator according to claim 21, wherein the release liner is slidably supported on the surface of the housing, wherein as the tab of the apex electrode is pulled in a direction substantially parallel to a plane of the release liner, the release liner is slid in the direction of the pull and separated from the apex electrode.

23. The defibrillator according to claim 22, wherein when the apex electrode is separate from the release liner, the tab of the sternum electrode is exposed.

* * * * *